United States Patent
Wolff

(10) Patent No.: US 9,585,568 B2
(45) Date of Patent: Mar. 7, 2017

(54) NONINVASIVE METHODS FOR DETERMINING THE PRESSURE GRADIENT ACROSS A HEART VALVE WITHOUT USING VELOCITY DATA AT THE VALVE ORIFICE

(76) Inventor: Steven D. Wolff, New York, NY (US)

(*) Notice: Subject to any disclaimer, the term of this patent is extended or adjusted under 35 U.S.C. 154(b) by 299 days.

(21) Appl. No.: 13/229,742

(22) Filed: Sep. 11, 2011

(65) Prior Publication Data
US 2013/0066229 A1    Mar. 14, 2013

(51) Int. Cl.
  *A61B 5/00*     (2006.01)
  *A61B 5/02*     (2006.01)
  *A61B 5/107*    (2006.01)

(52) U.S. Cl.
  CPC ........ *A61B 5/0044* (2013.01); *A61B 5/02028* (2013.01); *A61B 5/1079* (2013.01); *A61B 5/7239* (2013.01); *A61B 2576/00* (2013.01)

(58) Field of Classification Search
  USPC ................................. 600/485, 508, 526, 561
  See application file for complete search history.

(56) References Cited

U.S. PATENT DOCUMENTS

| | | | | |
|---|---|---|---|---|
| 5,178,153 | A * | 1/1993 | Einzig .................. | A61B 5/0261 356/477 |
| 5,997,883 | A * | 12/1999 | Epstein et al. ................ | 324/306 |
| 6,031,374 | A * | 2/2000 | Epstein et al. ................ | 324/306 |
| 6,149,595 | A * | 11/2000 | Seitz ...................... | A61B 8/065 600/438 |
| 6,176,832 | B1 * | 1/2001 | Habu et al. ................... | 600/485 |
| 6,245,027 | B1 * | 6/2001 | Alperin ......................... | 600/561 |
| 7,689,283 | B1 * | 3/2010 | Schecter .............. | A61B 5/0205 607/18 |
| 2005/0245809 | A1 * | 11/2005 | Wolff et al. ................... | 600/410 |
| 2006/0100499 | A1 * | 5/2006 | Shankaranarayanan et al. .............................. | 600/410 |
| 2006/0264764 | A1 * | 11/2006 | Ortiz-Burgos ................... | A61B 5/021 600/485 |
| 2006/0281375 | A1 * | 12/2006 | Jordan ........................... | 440/38 |
| 2008/0058656 | A1 * | 3/2008 | Costello et al. ............. | 600/508 |
| 2008/0132778 | A1 * | 6/2008 | Shankaranarayanan et al. .............................. | 600/413 |

(Continued)

OTHER PUBLICATIONS

Riggs, et al., "Measurement of Mitral Valve Orifice Area in Infants and Children by Two-Dimensional Echocardiography," 1983, J Am Coll Cardiol, vol. 3, p. 873-878.*

(Continued)

*Primary Examiner* — Daniel Cerioni
(74) *Attorney, Agent, or Firm* — Robert R. Deleault, Esq.; Mesmer & Deleault, PLLC

(57) ABSTRACT

Embodiments presented herein provide apparatus and methods for imaging-assisted determination of pressure gradient of blood flow across a valve orifice in a cardiovascular circuit without the use of velocity data measured at the valve orifice. An embodiment of the methods comprise creating an image of a valve orifice, creating a planimeter slice from the image of the valve orifice including a trace of the perimeter of the valve orifice, determining the valve orifice area by determining the area contained within the trace, determining the instantaneous flow rate through the valve orifice based on bulk flow data away from the valve, and determining the instantaneous pressure gradient across the valve orifice from the valve orifice area and the instantaneous flow rate.

19 Claims, 4 Drawing Sheets

(56) References Cited

U.S. PATENT DOCUMENTS

2009/0182287 A1* 7/2009 Kassab .................. 604/264
2009/0312648 A1* 12/2009 Zhang et al. ............ 600/483
2011/0275934 A1* 11/2011 Kassab .................. 600/431

OTHER PUBLICATIONS

Hakki et al., "A Simplified Valve Formula for the Calculation of Stenotic Cardiac Valve Areas," 1981, Circulation, 63: 1050-1055.*

* cited by examiner

NONINVASIVE METHODS FOR DETERMINING THE PRESSURE GRADIENT ACROSS A HEART VALVE WITHOUT USING VELOCITY DATA AT THE VALVE ORIFICE

FIELD

The present invention is related generally to the field of biological fluid flow. More particularly, the present invention relates to systems and methods that enable accurate determination of pressure gradient of fluid across an orifice within the body.

BACKGROUND

The aortic valve regulates the flow of blood between the left ventricle and the aorta. Typically the aortic valve comprises three leaflets. The leaflets open during systole to define a valve orifice to allow blood to pass from the left ventricle to the aorta. The valve orifice is the opening defined by the leaflets at the narrowest portion of an open aortic valve during systole. The leaflets close during diastole to prevent blood flow from the aorta back to the left ventricle. Aortic stenosis generally refers to an aortic valve wherein one or more leaflets become thickened and/or deformed due to calcification or other disease modality. The diseased leaflets may not open fully causing a restriction of blood flow and a higher pressure gradient across the smaller-than-normal valve orifice. The higher the pressure gradient across the valve orifice generally corresponds to a higher degree of aortic stenosis and therefore an indicator of a greater level of disease.

Table 1 shows how the typical mean pressure gradient varies with the severity of aortic stenosis.

TABLE 1

Severity of Aortic Stenosis

| Degree of aortic stenosis | Mean pressure gradient (mmHg) | Valve orifice area (cm$^2$) |
|---|---|---|
| Mild | <25 | >1.5 |
| Moderate | 25-40 | 1.0-1.5 |
| Severe | >40 | <1.0 |
| Critical | >70 | <0.6 |

From: http://en.wikipedia.org/wiki/Aortic_valve_stenosis

Quantifying the degree of aortic stenosis is critical to proper medical treatment of the patient. Mild aortic stenosis may be left untreated but monitored subject to the significance of any clinical symptoms. Moderate aortic stenosis may be treated with cholesterol lowering medications or other Pharmaceuticals. Severe to critical aortic stenosis may be surgically treated using methods such as catheter-based interventions and valve replacement but with the associated risks of surgical treatment.

The principle imaging modality for quantifying aortic stenosis is transthoracic echocardiography. The technique is noninvasive by using ultrasound to make images of the heart and to measure the velocity of blood flow at the valve orifice using Doppler data. The modified Bernoulli equation is commonly used to calculate the pressure gradient across a stenotic valve orifice where velocity at the valve orifice is known. The simplified general mathematical relationship is:

$$\text{Pressure Gradient (mm Hg)} = 4 * \text{Velocity}^2 \quad (EQ. 1)$$

Similarly, the transvalvular peak pressure gradient (PPG) at the valve orifice is estimated by measuring the peak velocity (Vp) of blood as it passes through the narrowest part of the valve orifice. The mathematical relationship is:

$$\text{PPG (mm Hg)} = 4 * Vp^2 \quad (EQ. 2)$$

In healthy individuals, Vp is typically about 1 m/s. In patients with mild aortic stenosis Vp is 2-3 m/sec. Peak velocities of 3-4 m/s are often found in patients with moderate aortic stenosis. Patients with severe aortic stenosis generally have peak velocities greater than 4 m/s.

Physicians sometimes also use the mean pressure gradient to determine the severity of aortic stenosis. The mean pressure gradient can be estimated by summing the instantaneous pressures during systole and dividing by the systolic ejection time. The instantaneous pressures are calculated from the instantaneous blood velocities at the valve orifice and the modified Bernoulli equation. Alternatively, the mean pressure gradient can be estimated by the following formula:

$$\text{mean } \Delta P(\text{mmHg}) = 2.4 \times v\left(\frac{m}{s}\right)^2_{max} \quad (EQ. 3)$$

Table 1 also lists a third parameter that physicians use to assess the severity of aortic stenosis, namely the aortic valve area (AVA), also referred herein as valve orifice area. Valve orifice area is defined as the area of the valve orifice on a planar slice through the narrowest portion of an open aortic valve during systole.

In echocardiography it is theoretically possible to measure the AVA directly by using planimetry on the valve orifice during systole when the aortic valve is open to the maximum extent. However, in most patients with aortic stenosis, the aortic valve is heavily calcified. Calcification blocks the ultrasound beam and prevents imaging so that it is usually impossible to accurately planimeter the valve orifice.

In practice, the determination of orifice area by echocardiography is usually calculated using the continuity equation. The basic premise of the continuity equation is that the volumetric flow rate, also referred herein as "flow rate", proximal to the area of aortic stenosis, such as in the left ventricular outflow tract (LVOT), must equal the volumetric flow rate at the valve orifice, assuming that blood is essentially an incompressible fluid. Commonly, the AVA is calculated using the following equation:

$$AVA = (Area_{LVOT}) * (VTI_{LVOT}/VTI_{AV}) \quad (EQ. 4)$$

In equation 4, the area of the LVOT is often expressed in cm$^2$. The area of the LVOT is determined by measuring the LVOT diameter ($D_{LVOT}$) and assuming that it is a circle ($Area_{LVOT} = 3.14 * D_{LVOT}^2/4$). The VTI (velocity time integral) is the integral of the velocity-time curve obtained from the ultrasound-derived Doppler signal of the volumetric flow rate of the blood in the respective locations.

The normal aortic valve area and the significance of aortic valve stenosis depend in part on the size of the patient. Some investigators will divide the aortic valve area by the body surface area of the patient to determine the aortic valve area index (AVAI). Body surface area is calculated from a formula that uses the height and weight of the person as inputs. A scale of degree of severity based on the aortic valve area index (AVAI) has been used by some in the art.

The use of transthoracic echocardiography for quantifying aortic stenosis in accordance with the three methods discussed above introduces errors and assumptions that may not provide accurate determination of the pressure gradient across a stenotic aortic valve. These errors and assumptions include, but are not limited to, inaccurate average or peak velocity measurements at the valve orifice and inaccurate body surface assumptions.

MRI may be used in an analogous manner to echocardiography. Namely, velocities of blood may be imaged by MRI and used to calculate a peak pressure gradient using the modified Bernoulli equation, and velocities may be used to calculate the aortic valve area using the continuity equation. However, MRI has different strengths and weaknesses than echocardiography. While MRI can measure velocities with phase-contrast techniques, performing this method often adds to the total cardiac MRI examination time. In addition, there are a number of sources of errors to the velocity measurement. Sources of error include turbulent flow, partial volume averaging, flow not perpendicular to the imaging slice, and baseline offset errors due to eddy currents.

For MRI to make the same measurements in an analogous manner to echocardiography, the user typically will acquire a series of contiguous parallel imaging planes starting at the left ventricular outflow tract and extending through the aortic valve leaflets. The slices are oriented substantially perpendicular to the direction of blood flow, A phase-contrast imaging sequence is used to capture velocity data throughout the cardiac cycle. After the images are acquired, the user will typically select the phase of the cardiac cycle where blood flow is maximal. Using a region of interest, the user will determine the blood velocity within the left ventricular outflow tract (VpLvor). The user will then determine the peak velocity ($Vp_Av$) of blood flow at the valve orifice. According to the simplified Bernoulli equation, the peak pressure gradient will be $4*Vp^2$. According to the continuity equation, the aortic valve area will be AreaLvoi*(VpLvoiN-pAv).

Similar to transthoracic echocardiography, the use of MRI to provide velocity data for quantifying aortic stenosis in accordance with the method discussed above introduces errors and assumptions that may not provide accurate determination of the pressure gradient across a stenotic aortic valve.

For patients in whom echocardiography is unable to unambiguously determine the severity of the aortic stenosis, and for those patients where the clinical symptoms do not correlate with the echocardiographic findings, cardiac catheterization is often used to determine the severity of the aortic stenosis. In this procedure a catheter is introduced into a peripheral artery and advanced retrograde through the aorta until the tip traverses the aortic valve. With this procedure, a physician can directly measure the pressure gradient across the valve orifice. Using a catheter based thermodilution technique, cardiac output can also be estimated. The aortic valve area may be estimated using the Gorlin equation:

$$\text{Aortic Valve Area (cm}^2\text{)} = \frac{\text{Cardiac Output}\left(\frac{\text{ml}}{\text{min}}\right)}{\text{Heart Rate}\left(\frac{\text{beats}}{\text{min}}\right) \times \text{Systolic Ejection Period(s)} \times 44.3 \times \sqrt{\text{mean Gradient (mmHg)}}} \quad \text{(EQ. 5)}$$

or the even simpler Haaki equation:

$$\text{Valve Area (cm}^2\text{)} = \frac{\text{Cardiac Output}\left(\frac{\text{liter}}{\text{min}}\right)}{\sqrt{\text{mean Gradient (mmHg)}}} \quad \text{(EQ. 6)}$$

Although it is considered the "gold standard" test, catheterization is an invasive procedure and carries potentially serious risks to the patient such as infection, aortic dissection (a tear within the wall of the aorta), and stroke. Cardiac catheterization introduces its own errors and assumptions that may not provide accurate determination of the pressure gradient across a stenotic aortic valve.

An inaccurate pressure gradient determination may directly impact the treatment plan for the patient. If the pressure gradient is under predicted, a lower degree of severity of disease will be predicted, resulting in, such as, but not limited to, a delay in or less aggressive treatment intervention possibility leading to continued or worsening patient morbidity. If the pressure gradient is over predicted, a higher degree of severity of disease will be predicted, resulting in, such as, but not limited to, an over aggressive treatment with its underlying increase of risks to the patient and increased costs that may not be necessary.

It would therefore be desirable to provide non-invasive apparatus and methods for more accurately determining the pressure gradient across a cardiovascular orifice, such as, but not limited to, a stenotic aortic valve.

SUMMARY

Embodiments presented herein provide apparatus and methods for imaging-assisted determination of pressure gradient of fluid across an orifice in a cardiovascular circuit without the use of velocity data measured at the orifice. An embodiment of a method for obtaining a pressure gradient across an orifice in a cardiovascular circuit through which blood is flowing, comprises, using MRI data, creating an image of the orifice, measuring the orifice area of the orifice without using velocity data measured at the orifice, determining the instantaneous flow rate through the valve orifice based on bulk flow data measured away from the valve, and determining the instantaneous pressure gradient across the orifice from the orifice area and the instantaneous flow rate.

In accordance with an embodiment, creating an image of the orifice comprises creating a three-dimensional image of a portion of the anatomy including the orifice. In accordance with an embodiment, creating a planimeter slice comprises finding a plane within the three-dimensional image that is perpendicular to the blood flow where the orifice is the narrowest.

In accordance with another embodiment, a computer-readable medium having computer-executable instructions for performing a method for obtaining a pressure gradient across an orifice in a cardiovascular circuit through which blood is flowing comprises, using MRI data, creating an image of the orifice, measuring the orifice area of the orifice without using velocity data measured at the orifice, determining the instantaneous flow rate through the valve orifice based on bulk flow data measured away from the valve, and determining the instantaneous pressure gradient across the orifice from the orifice area and the instantaneous flow rate.

BRIEF DESCRIPTION OF THE DRAWINGS

Embodiments are illustrated by way of example and not by way of limitation in the figures of the accompanying drawings, in which like references may indicate similar elements throughout the various figures unless otherwise specified.

DETAILED DESCRIPTION

Figure 1:
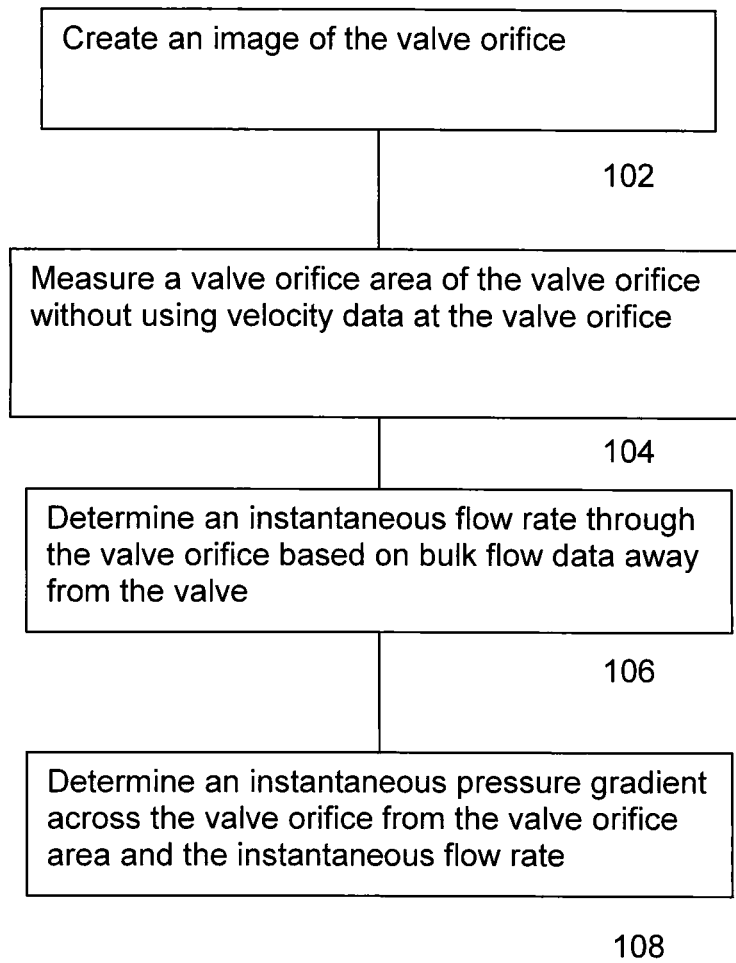
FIG. 1 is a flow chart of a method of determining pressure gradient across an orifice, in accordance with an embodiment.

In the following description, embodiments of apparatus and methods will be disclosed. For purposes of explanation, specific numbers, materials, and/or configurations are set forth in order to provide a thorough understanding of the embodiments. However, it will also be apparent to those skilled in the art that the embodiments may be practiced without one or more of the specific details, or with other approaches, materials, components, etc. In other instances, well-known structures, materials, and/or operations are not shown and/or described in detail to avoid obscuring the embodiments. Accordingly, in some instances, features are omitted and/or simplified in order to not obscure the disclosed embodiments. Furthermore, it is understood that the embodiments shown in the figures are illustrative representations and are not necessarily drawn to scale. Also, it is to be understood that the phraseology and terminology employed herein is for the purpose of description and should not be regarded as limiting.

Reference throughout this specification to "one embodiment" or "an embodiment" means that a particular feature, structure, characteristic, or method described in connection with the embodiment is included in at least one embodiment of claimed subject matter. Thus, the appearances of the phrase "in one embodiment" or "an embodiment" in various places throughout this specification are not necessarily all referring to the same embodiment. Furthermore, the particular features, structures, characteristics, or methods may be combined in one or more embodiments.

Reference will now be made to embodiments illustrated in the drawings and specific language which will be used to describe the same. It will nevertheless be understood that no limitation of the scope of the invention is thereby intended. Alterations and further modifications of the illustrated embodiments and further applications of the principles of the invention, as would normally occur to one skilled in the art to which the invention relates, are also within the scope of the invention.

For the purposes of the subject matter disclosed herein, reference to the term "MRI" is used herein as an abbreviation for "magnetic resonance imaging". The terms "MRI" and "magnetic resonance imaging" are used interchangeably in the following.

Reference throughout this specification to "across" in reference to fluid flowing across a valve orifice as used herein refers to blood flow through the valve orifice.

Reference throughout this specification to "pressure gradient" in reference to across a valve orifice as used herein refers to a pressure drop of the blood as it passes through the valve orifice.

Reference throughout this specification to "flow" and "flow rate" refer to instantaneous flow rate.

Reference to the term "stenosis" refers to an abnormal narrowing of a tubular structure in the body, such as, but not limited to, a blood vessel, heart valve, and other tubular organs. A stenosis restricts the flow of blood therethrough. For example, an aortic stenosis refers to an abnormal narrowing of the valve orifice of the aortic valve during systole.

Reference to the term "valve orifice" when determining pressure gradient across the valve refers to the narrowest portion of the valve at maximum pressure during systole. It is understood that generally, the narrowest opening is defined by the leaflet edges, but not exclusively so.

Reference to the term "planimetry" refers to a technique for determining the area of an arbitrary three-dimensional shape. In reference to determining valve orifice area, the valve orifice may be directly measured from two-dimensional imaging or constructed from three-dimensional volumetric imaging of the valve. Related to three-dimensional volumetric imaging, planar slices through the volume and substantially perpendicular to the flow are made to identify the narrowest opening of the valve. The perimeter of the valve is projected onto and traced on a plane and the area inside the trace is calculated to determine the valve orifice area. It is understood that the tracing of the valve perimeter onto a plane may be performed by any suitable means, including, but not limited to manual tracing or digitized tracing by the user, and digitized computationally using a computer.

A "computer program" as referred to herein relates to an organized list of instructions that, if executed, results in or causes a computer, computing device and/or machine to behave in a particular manner. Here, for example, a computer program may comprise machine-readable instructions that are executable to perform one or more desired tasks. In one particular embodiment, although claimed subject matter is not limited in this respect, a computer program may define input data and output data such that execution of the program may provide output data based, at least in part, on the input data. However, these are merely examples of a computer program and claimed subject matter is not limited in these respects.

Block and flow diagrams are presented in figures to describe the subject matter. However, claimed subject matter is not limited in scope to a particular example presented in the figures. For example, for flow diagrams presented herein, the order in which blocks are presented does not necessarily limit claimed subject matter to any particular order. Additionally, intervening blocks not shown may be employed without departing from the scope of claimed subject matter. Likewise, flow diagrams depicted herein may, in alternative embodiments, be implemented as a combination of hardware, software and/or firmware, such as part of a computer or computing system.

It will be understood that each block of the flowchart illustration, and combinations of blocks in the flowchart illustration, can be implemented by computer program instructions. These program instructions may be provided to a processor to produce a machine, such that the instructions, which execute on the processor, create means for implementing the actions specified in the flowchart block or blocks. The computer program instructions may be executed by a processor to cause a series of operational steps to be performed by the processor to produce a computer implemented process such that the instructions, which execute on the processor to provide steps for implementing the actions specified in the flowchart block or blocks. The computer program instructions may also cause at least some of the operational steps shown in the blocks of the flowchart to be performed in parallel. Moreover, some of the steps may also be performed across more than one processor, such as might arise in a multi-processor computer system. In addition, one or more blocks or combinations of blocks in the flowchart illustrations may also be performed concurrently with other blocks or combinations of blocks, or even in a different sequence than illustrated without departing from the scope or spirit of the embodiments.

Accordingly, blocks of the flowchart illustrations support combinations of means for performing the specified actions, combinations of steps for performing the specified actions and program instruction means for performing the specified actions. It will also be understood that each block of the flowchart illustrations, and combinations of blocks in the flowchart illustrations, can be implemented by special purpose hardware-based systems which perform the specified actions or steps, or combinations of special purpose hardware and computer instructions.

Briefly stated, embodiments provided herein are directed to systems and methods for imaging-assisted determination of pressure gradient of fluid across an orifice in a cardiovascular circuit without the use of velocity data measured at the orifice. MRI imaging techniques may be used to directly image the orifice where the orifice may be calcified precluding imaging via echocardiography techniques. Instantaneous flow rate data may be determined without using velocity data measured at the orifice. This precludes errors that, among other things, may be induced in the measurement of velocity data and using simplified equations for the determination of the instantaneous flow rate using velocity data measured at the orifice.

For convenience and simplicity of explanation, by way of example, but not limited thereto, embodiments herein will present the application of the systems and methods for the determination of pressure gradient across a valve orifice of a stenotic aortic valve. It is appreciated that the systems and methods presented herein may be utilized to determine pressure gradient across other cardiovascular orifices within a body through which fluid passes.

Embodiments provided herein are directed to systems and methods for MRI-assisted determination of pressure gradient of fluid across an orifice in a cardiovascular circuit without the use of velocity data. Embodiments herein will present the application of the systems and methods for the determination of pressure gradient across a stenotic aortic valve by way of example, but not limited there to. It is appreciated that the systems and methods presented herein may be utilized to determine pressure gradient across other orifices in a cardiovascular circuit.

In accordance with an embodiment of a method, illustrated by the flow chart of FIG. 1, direct imaging of a valve is made using non-invasive imaging techniques that are operable to image calcified tissue. Examples of suitable non-invasive imaging techniques include, but are not limited to, MRI and CT (computed tomography). A non-invasive imaging technique is used to locate the narrowest opening of the valve when at maximum systole so as to identify the valve orifice 102. From the direct imaging of the valve orifice a planimeter slice that is substantially perpendicular to the flow is created including a trace of the perimeter of the valve orifice 104. An orifice area is determined by computing the area bounded by the trace 406. Instantaneous volumetric flow rate through the valve orifice is measured using imaging techniques 108. The pressure gradient across the valve orifice is calculated from the orifice area and the instantaneous flow rate 110.

Figure 2:
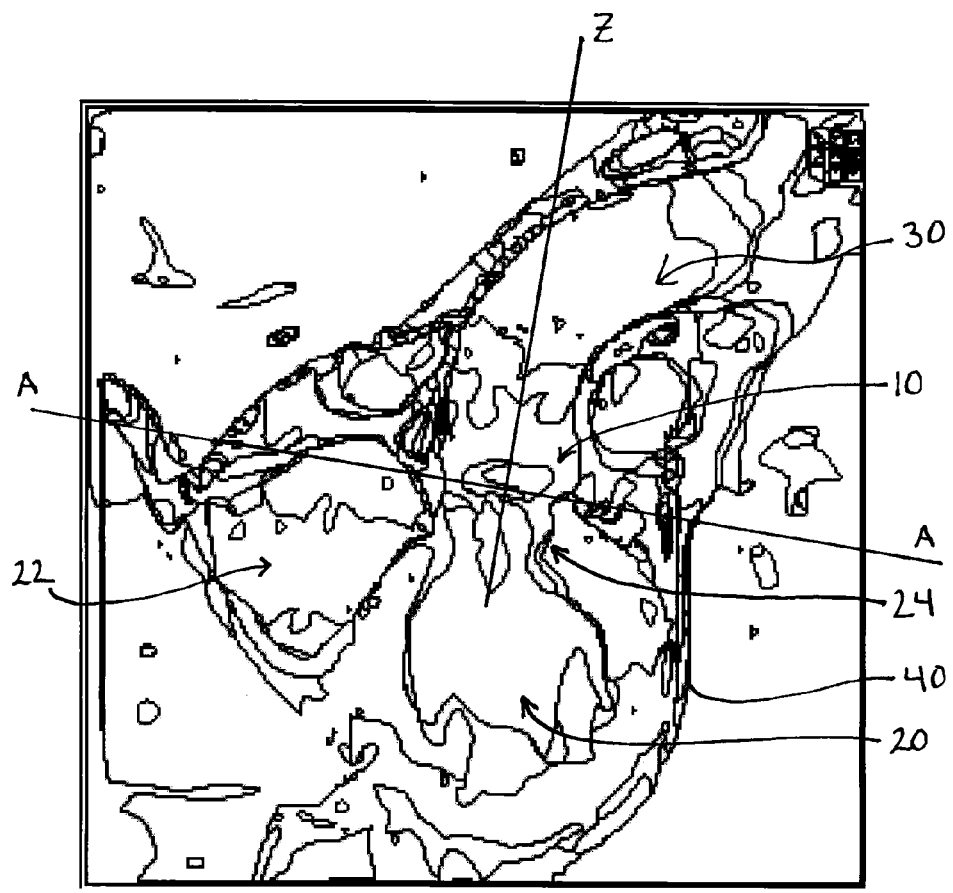
FIG. 2 is an MRI cine frame showing a side view of a human heart.

In accordance with an embodiment, a method for determining the aortic valve area comprises using MRI to directly image the valve and using planimetry to determine the cross sectional area of the valve orifice. FIG. 2 is an MRI cine frame showing a side view of a human heart 40, including the right atrium 22, left ventricle 20, left ventricle outflow tract 24, aortic valve 10, and aorta 30 during diastole when the aortic valve 10 is closed. The Z-axis of the aortic valve 10 is indicated by the line Z as shown which is substantially parallel to the direction of blood flow. At a time phase in systole where the aortic valve 10 is maximally open, referred herein as maximum systole, a cine image slice, which is a planar slice, is acquired perpendicular to the Z-axis and at a location where the valve opening is narrowest so as to identify the valve orifice 12.

Figure 3:
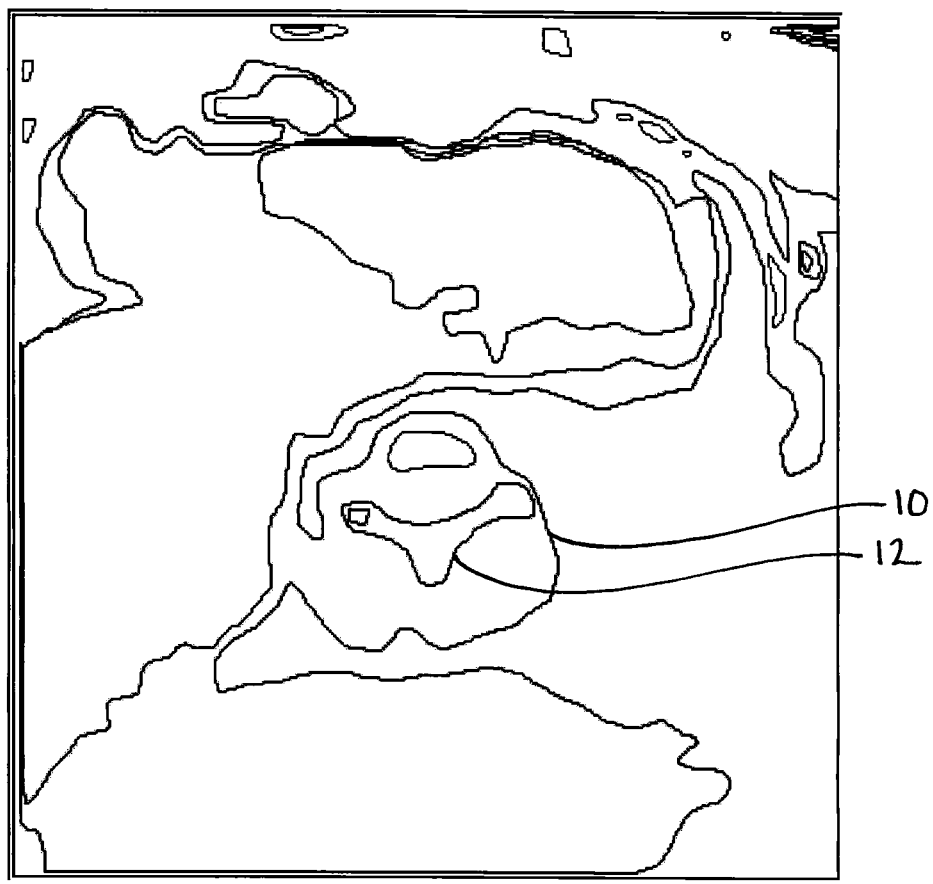
FIG. 3 is an MRI cine frame acquired perpendicular to the Z-axis of the aortic valve at the valve orifice.

FIG. 3 is an MRI cine frame acquired perpendicular to the Z-axis of the aortic valve 10 at the valve orifice 12. A plurality of parallel cine image slices perpendicular to the Z-axis along the aortic valve 10 during maximum systole may be required so as to capture the appropriate image where the valve orifice 12 is narrowest.

Figure 4:
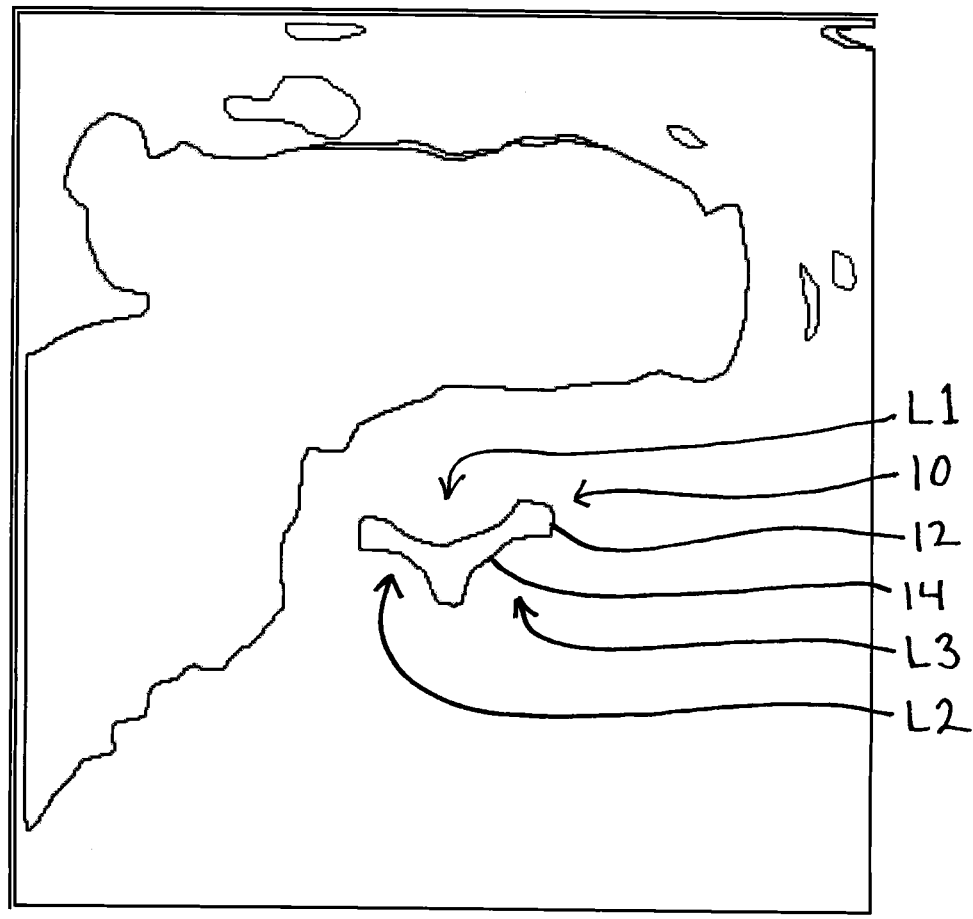
FIG. 4 is a planimetry slice corresponding to the cine slice of FIG. 3 showing a tracing of the orifice perimeter.

FIG. 4 is a planimetry slice corresponding to the cine slice of FIG. 3 showing the aortic valve 10 with corresponding three leaflets L1, L2, L3 and a trace 14 of the valve orifice perimeter. The trace 14 defines the valve orifice 12 such that the valve orifice area may be readily determined from the trace 14.

The instantaneous pressure gradient across the valve orifice may be determined using the measured orifice area, also referred to as the actual valve area (AVA), using the following relationship:

$$\text{Instantaneous Pressure} = (\text{Flow}/\text{AVA})^2 \qquad (\text{EQ. 7})$$

where AVA is the actual valve area and Flow is the instantaneous flow rate.

Instantaneous flow rate may be determined using a number of methods. In accordance with an embodiment, MRI may be used to acquire a series of cine slices through the left ventricle 20 shown in FIG. 2 over a period of time during systole. The flow volume within an interval of time, for example, within the systolic portion of the cardiac cycle, is determined. The derivative of this curve is the flow versus time. By assuming that the entire fluid output of the left ventricle 20 passes through the aortic valve 10 and thus the valve orifice 12 during each systolic period, the flow versus time value may be used to determine the instantaneous flow rate across the valve orifice 12. In accordance with embodiments, determining the instantaneous flow rate comprises acquiring a series of cine slices through the left or right ventricle, creating a volume versus time curve, and taking the derivative of the volume versus time curve to derive instantaneous flow rate.

The assumption that the entire output of the left ventricle 20 passes through the aortic valve 10 may not be accurate, such as, but not limited to, for patients with significant mitral regurgitation or a ventricular septal defect, among other things. In accordance with embodiments, a method to determine the instantaneous flow rate across the valve orifice 12 of the aortic valve 10 includes acquiring a single phase contrast cine slice perpendicular to the left ventricular outflow tract (LVOT) 24 as shown in FIG. 1. From this single phase contrast cine slice a measurement of instantaneous flow rate is calculated using methods as is known in the art.

Where obtaining data in the LVOT 24 is problematic, such as where there may be an obstruction in the LVOT 24, phase contrast flow data from other places, such as, but not limited to, the right ventricular outflow tract (RVOT), the ascending aorta, or the main pulmonary artery may be used to calculate the instantaneous flow rate using methods as is known in the art. In accordance with embodiments, determining the instantaneous flow rate through the valve orifice based on bulk flow data away from the valve comprises acquiring a single phase contrast cine slice perpendicular to the blood flow through the left ventricular outflow tract, right ventricular outflow tract, main pulmonary artery, or ascending aorta to obtain phase contrast flow data, and using the phase contrast flow data to determine instantaneous flow rate.

In accordance with other embodiments, the accuracy of the pressure assessment may be enhanced by modifying equation 7 to take into account the viscosity of the blood which is substantially linearly related to the hematocrit, as well as the shape of the stenotic aortic valve (e.g. eccentric vs. circular).

Methods in accordance with embodiments are provided for determining instantaneous pressure across a dynamic orifice through which blood is flowing without using velocity data measured at the orifice. MRI may be used to determine the instantaneous flow rate and the orifice area, from which the instantaneous pressure may be calculated. Since velocity measurements at the orifice are not used, the errors and limitations associated with velocity measurements as explained previously are not factors in the determination of instantaneous pressure across the orifice.

Methods in accordance with embodiments are provided for obtaining selected instantaneous area measurements for a dynamic orifice through which blood is flowing, for determining instantaneous flow rates of blood passing through such a dynamic orifice, and for obtaining the pressure gradient through the dynamic orifice.

Beyond the presented application for aortic valve stenosis, embodiments presented herein may be applied to other diseases associated with flow through an orifice in a cardiovascular circuit; for example, flow through each of the four heart valves, as well as valvular stenosis, septal defects with shunt flow, and peripheral vascular disease with vessel obstruction. Valvular stenosis refers to restricted forward flow due to a condition that prevents the valve from opening completely. A septal defect refers to a pathologic orifice in the septum that separates the right and the left side of the heart. In particular, accurate noninvasive measurement of stenotic valve opening areas based on planimetry of image data would critically improve diagnosis and treatment of stenotic valve disease.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

I claim:

1. A method for a computer-assisted determination of an instantaneous pressure gradient across an open valve orifice in a cardiovascular circuit through which blood is flowing, comprising:
    creating a series of imaging slices during a period of time of the open valve orifice using a non-invasive, computer-based imaging hardware selected from the group consisting of MRI and CT;
    selecting an image from the series of images of the open valve orifice;
    measuring a valve orifice area of the open valve orifice from the image;
    determining an instantaneous flow rate through the open valve orifice without using velocity data at the open valve orifice, the instantaneous flow rate being based on a flow volume through a left or right ventricle wherein the flow volume is determined from the series of imaging slices through the left or right ventricle, creating a volume versus time curve for the left or right ventricle, and taking the derivative of the volume versus time curve to derive instantaneous flow rate; and
    determining an instantaneous pressure gradient across the open valve orifice from the valve orifice area and the instantaneous flow rate;
    wherein the method for a computer-assisted determination of the instantaneous pressure gradient across the open valve orifice in a cardiovascular circuit does not use velocity data.

2. The method of claim 1, wherein the selecting the image of the valve orifice comprises creating a two-dimensional image, and wherein measuring the valve orifice area of the open valve orifice comprises:
    creating a planimeter slice from the two-dimensional image;
    creating a trace of a perimeter of the open valve orifice on the planimeter slice; and
    determining the valve orifice area by determining the area contained within the trace of the perimeter of the open valve orifice.

3. The method of claim 1, wherein creating the series of imaging slices of the open valve orifice comprises creating a three-dimensional volume image of a portion of the left or right ventricle including the open valve orifice; and
    wherein measuring the valve orifice area of the open valve orifice comprises:
    creating a planimeter slice by finding a plane within the three-dimensional volume image that is perpendicular to blood flow where the open valve orifice is narrowest.

4. The method of claim 1, wherein measuring the valve orifice area of the open valve orifice comprises:
    selecting a time phase in systole where the open valve orifice is maximally open;
    creating a planimeter slice from the image wherein the planimeter slice is substantially perpendicular to the direction of blood flow at a location where the open valve orifice is narrowest; and
    creating a trace of the perimeter of the open valve orifice on the planimeter slice; and
    determining the valve orifice area by determining the area contained within the trace of the perimeter of the open valve orifice.

5. The method of claim 1, wherein creating an image of the open valve orifice on a planar slice comprises imaging a valve orifice on a planar slice using MRI.

6. The method of claim 1, wherein creating an image of the open valve orifice on a planar slice comprises imaging the open valve orifice on a planar slice using CT.

7. The method of claim 1, wherein creating the a series of imaging slices through a left or right ventricle comprises acquiring a series of cine slices through the left or right ventricle.

8. The method of claim 1, wherein determining the instantaneous pressure gradient across the open valve orifice from the valve orifice area and the instantaneous flow rate comprises calculating the instantaneous pressure gradient as equal to the square of the quotient of instantaneous flow rate divided by the valve orifice area.

9. The method of claim 1 wherein creating the series of images of the open valve orifice comprises:
performing at least an imaging sequence for imaging a size of an actual valve area defined by a perimeter of open valve leaflets during peak systole.

10. A computer-readable medium having computer-executable instructions for performing a method for a computer-assisted determination of a pressure gradient across an open valve orifice in a cardiovascular circuit through which blood is flowing, comprising:
creating a series of imaging slices during a period of time of the open valve orifice using a non-invasive, computer-based imaging hardware selected from the group consisting of MRI and CT;
selecting an image from the series of images of the open valve orifice;
measuring a valve orifice area of the open valve orifice;
determining an instantaneous flow rate through the open valve orifice without using velocity data at the open valve orifice, the instantaneous flow rate being based on a flow volume through a left or right ventricle wherein the flow volume is determined from the series of imaging slices through the left or right ventricle, creating a volume versus time curve for the left or right ventricle, and taking the derivative of the volume versus time curve to derive instantaneous flow rate; and
determining an instantaneous pressure gradient across the open valve orifice from the valve orifice area and the instantaneous flow rate;
wherein the method for a computer-assisted determination of the instantaneous pressure gradient across the open valve orifice in a cardiovascular circuit does not use velocity data.

11. The computer-readable medium of claim 10, wherein the selecting the image of the open valve orifice comprises creating a two-dimensional image, and wherein measuring the valve orifice area of the open valve orifice comprises:
creating a planimeter slice from the image;
creating a trace of a perimeter of the open valve orifice on the planimeter slice; and
determining the orifice area by determining the area contained within the trace of the perimeter of the orifice.

12. The computer-readable medium of claim 10, wherein creating the series of imaging slices of the open valve orifice comprises creating a three-dimensional volume image of a portion of the left or right ventricle including the orifice; and
wherein measuring the valve orifice area of the open valve orifice comprises creating a planimeter slice by finding a plane within the three-dimensional volume image that is perpendicular to blood flow where the open valve orifice is narrowest.

13. The computer-readable medium of claim 10, wherein measuring the valve orifice area of the open valve orifice comprises:
selecting a time phase in systole where the open valve orifice is maximally open;
creating a planimeter slice from the image wherein the planimeter slice is substantially perpendicular to the direction of blood flow at a location where the open valve orifice is narrowest; and
creating a trace of a perimeter of the open valve orifice on the planimeter slice; and
determining the valve orifice area by determining the area contained within the trace of the perimeter of the open valve orifice.

14. The computer-readable medium of claim 10, wherein creating an image of the open valve orifice on a planar slice comprises imaging the open valve orifice on a planar slice using MRI.

15. The computer-readable medium of claim 10, wherein creating an image of the open valve orifice on a planar slice comprises imaging the open valve orifice on a planar slice using CT.

16. The computer-readable medium of claim 10, wherein creating the series of imaging slices through a left or right ventricle comprises acquiring a series of cine slices through the left or right ventricle.

17. The computer-readable medium of claim 10, wherein determining the instantaneous pressure gradient across the open valve orifice from the valve orifice area and the instantaneous flow rate comprises calculating the instantaneous pressure gradient as equal to the square of the quotient of instantaneous flow rate divided by the valve orifice area.

18. The method of claim 1, wherein determining the instantaneous pressure gradient across the open valve orifice includes determining the instantaneous pressure gradient using the following equation:

$$\text{Instantaneous Pressure Gradient} = (\text{Flow}/\text{AVA})^2$$

where Flow is the instantaneous flow rate, and
AVA is the actual valve area.

19. The computer-readable medium of claim 10, wherein determining the instantaneous pressure gradient across the open valve orifice includes determining the instantaneous pressure gradient using the following equation:

$$\text{Instantaneous Pressure Gradient} = (\text{Flow}/\text{AVA})^2$$

where
Flow is the instantaneous flow rate, and
AVA is the actual valve area.

* * * * *